United States Patent
Liu et al.

(10) Patent No.: US 7,468,130 B2
(45) Date of Patent: *Dec. 23, 2008

(54) ORGANOSILANES AND SUBSTRATES COVALENTLY BONDED WITH SAME AND METHODS FOR SYNTHESIS AND USE SAME

(75) Inventors: Xiaodong Liu, Cupertino, CA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 338 days.

This patent is subject to a terminal disclaimer.

(21) Appl. No.: 11/059,179

(22) Filed: Feb. 15, 2005

(65) Prior Publication Data

US 2006/0180549 A1    Aug. 17, 2006

(51) Int. Cl.
*B01D 15/08* (2006.01)

(52) U.S. Cl. .................. 210/198.2; 210/502.1; 210/635; 210/656

(58) Field of Classification Search ............ 210/502.1, 210/635, 656, 658, 659, 198.2; 502/401
See application file for complete search history.

(56) References Cited

U.S. PATENT DOCUMENTS

| | | | | |
|---|---|---|---|---|
| 4,177,038 A * | 12/1979 | Biebricher et al. | ............. | 8/192 |
| 4,213,860 A * | 7/1980 | Tsibris | ........................ | 210/656 |
| 4,322,310 A * | 3/1982 | House | ........................ | 252/184 |
| 4,415,631 A * | 11/1983 | Schutijser | ................... | 428/405 |
| 4,431,546 A * | 2/1984 | Hughes et al. | .............. | 210/656 |
| 4,627,919 A * | 12/1986 | Yuki | ........................... | 210/656 |
| 4,650,784 A * | 3/1987 | Ramsden et al. | ............. | 502/407 |
| 4,830,921 A * | 5/1989 | Kitayama et al. | ........... | 428/406 |
| 4,837,348 A * | 6/1989 | Stolowitz et al. | ................ | 556/9 |
| 4,883,598 A * | 11/1989 | Riethorst et al. | ............. | 210/656 |
| 4,985,144 A * | 1/1991 | Quentin-Millet et al. | . | 210/198.2 |
| 5,043,062 A * | 8/1991 | Bale et al. | ................. | 210/198.2 |
| 5,045,190 A * | 9/1991 | Carbonell et al. | ......... | 210/198.2 |
| 5,137,627 A * | 8/1992 | Feibush | .................... | 210/198.2 |
| 5,149,426 A * | 9/1992 | Watabe et al. | ............. | 210/198.2 |
| 5,240,602 A * | 8/1993 | Hammen | .................. | 210/198.2 |
| 5,277,813 A * | 1/1994 | Feibush et al. | ............ | 210/502.1 |
| 5,868,938 A * | 2/1999 | Bomer et al. | ............... | 210/656 |
| 6,020,448 A * | 2/2000 | Jenkner et al. | ................. | 528/26 |
| 6,645,378 B1 * | 11/2003 | Liu et al. | .................. | 210/198.2 |

(Continued)

FOREIGN PATENT DOCUMENTS

EP    0 885 895 A2    5/1998

(Continued)

OTHER PUBLICATIONS

Snyder (Introduction to Modern Liquid Chromatography, John Wiley & Sons, New York 1979, pp. 272-275).*

(Continued)

*Primary Examiner*—Ernest G Therkorn
(74) *Attorney, Agent, or Firm*—Morgan, Lewis & Bockius LLP; David J. Brezner

(57) ABSTRACT

The present invention provides novel silicon compounds, methods for making these novel silicon compounds, compositions comprising these novel silicon compounds attached to substrates, methods for attaching the novel silicon compounds to substrates and methods for using the compositions in a variety of chromatographic applications.

12 Claims, 10 Drawing Sheets

U.S. PATENT DOCUMENTS 6,949,186 B2 * 9/2005 Liu et al. .............. 210/198.2
7,074,491 B2 * 7/2006 Liu et al. .............. 428/447

FOREIGN PATENT DOCUMENTS

EP  0 885 895 A3  5/1998

OTHER PUBLICATIONS

Berendsen (Journal of Chromatography, 1980, 196, 21-37).*
McDonald (Solid Phase Applications, 1995, p. 23).*
Calas, R., "A trimethoxysiyloamine and a trimethyoxysilyl ketone derived from 10-undecenoic acid," *Rev. Frac. Corps Gras* 3:5-9 (1956).
Speier, J., et al., "Synthesis of (3-aminoalkyl) silicon compounds," *J. Org. Chem.* 36(21):3120-3126 (1971).
Abstract of Japan Patent 5602 7648 Mar. 18, 1981.
Abstract of Zhumal Obshchei Khimii (USSR) 38(11):2582-2585 (1968).
Neue, U., *HPLC Columns: Theory, Technology and Practice*, pp. 183-249, John Wiley & Sons, Ltd.: New York, NY (Jul. 1997).
O'Gara, J., et al., "Embedded-polar-group bonded phases for high performance liquid chromatography," *LC-GC* 19(6):632-641 (Jun. 2001).
Schmitt, T., *Analysis of Surfactants*, 2nd ed., pp. 197-292, Marcel Dekker, Inc.:New York, NY (2001).

* cited by examiner

ORGANOSILANES AND SUBSTRATES COVALENTLY BONDED WITH SAME AND METHODS FOR SYNTHESIS AND USE SAME

1. FIELD

The present invention relates generally to novel silicon compounds, methods for making these novel silicon compounds, compositions comprising these novel silicon compounds attached to substrates, methods for attaching the novel silicon compounds to substrates and methods for using the compositions in a variety of chromatographic applications.

2. BACKGROUND

Conventional reversed phase silica columns (e.g., ODS) are widely used as general-purpose stationary phases for chromatographic separations (Neue, "HPLC Columns—Theory, Technology, and Practice," WILEY-VCH, New York, 1997, 183-203). However, some drawbacks, including, for example, "phase collapse" (i.e., dewetting) in highly aqueous environments, weak retention of ionic compounds and residual silanol activity which leads to peak tailing of basic analytes prevent employment of conventional reverse phase silica columns in certain applications.

Polar-embedded phases improve the peak shape of basic analytes and enable operation of reverse phase HPLC columns in highly aqueous environments (O'Gara et al., *LC-GC* 2001, 19 (6):632-641). Commonly used polar groups include, for example, amides, ureas, ethers and carbamates. In general, polar-embedded phases provide superior peak shapes of basic analytes and are more compatible with highly aqueous environments when compared to general purpose reverse phases. Further, polar embedded phases often have selectivities which are substantially different from those exhibited by conventional C-18 packings.

Surfactants are important components of a variety of consumer, industrial, agricultural and pharmaceutical products. Surfactant analysis is often complicated by the presence of mixtures which are difficult to resolve using conventional chromatography. Surfactants have been analyzed by liquid chromatography on reversed-phase columns (e.g., C18, C8, cyano, phenyl, etc.), normal phase columns, ion-exchange columns and size-exclusion columns (Schmitt, "Analysis of Surfactants," 2$^{nd}$ edition, Marcel Dekker, Inc, New York, 2001, 197-292). C18 columns provide reasonable separation, peak efficiency and asymmetry, especially for anionic surfactants. However, the presence of underivatized silanols on silica-based reversed-phase columns often prevents satisfactory resolution of cationic surfactants. For example, C18 reversed phase columns fail to separate individual oligomers of polyethylene glycol (PEG) based surfactants. In addition, because of "de-wetting" caused by necessary usage of high aqueous mobile phases, conventional high-density C18 columns are unsuitable for analysis of highly hydrophilic hydrotopes, (e.g., sodium naphthalene sulfonate and xylene sulfonate). Despite the availability of a variety of HPLC columns to analyze a wide range of surfactants using a plurality of different conditions, no single column can be used to separate cationic, nonionic, and anionic surfactants in a single run using simple and volatile, mass spectroscopy compatible, mobile phases.

Accordingly, what is needed are novel silane compounds which have both hydrophobic and polar functionality, substrates functionalized with these new silane compounds and the use of these novel functionalized substrates to simultaneously separate cationic, nonionic and anionic surfactants.

3. SUMMARY

The present invention satisfies these and other needs by providing a new class of silane compounds, which have hydrophobic and polar functionality, substrates functionalized with these new silane compounds and the use of these novel functionalized substrates to simultaneously separate cationic, nonionic, and anionic surfactants.

In one aspect, a compound described by Formula (I) is disclosed:

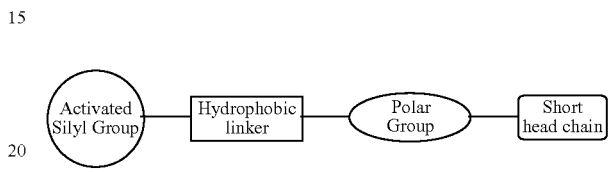

I or salts, solvates or hydrates thereof. The compound of Formula (I) has at least one activated silyl group (e.g., $Si(OMe)_3$, —$SiMe(OMe)_2$, —$SiMe_2(OMe)$, —$Si(OEt)_3$, —$SiMe(OEt)_2$, —$SiMe_2(OEt)$, —$SiMe_2NMe_2$, —$SiCl_3$, etc.), at least one polar group (e.g., amide, sulfonamide, carbamate, urea, ester, etc.) and a short head chain (e.g., ($C_1$-$C_6$) alkyl) connected to the polar group.

In another aspect, a compound of structural Formula (II) is provided:

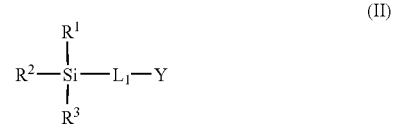

(II)

or salts, solvates or hydrates thereof
wherein:
$R^1$, $R^2$ and $R^3$ are independently alkyl, alkoxy, alkoxycarbonyl, alkylsulfonyloxy, amino, aryl, aryloxycarbonyl, arylsulfonyloxy, halo or hydroxyl, optionally substituted with one or more $R^{12}$ groups, provided that at least one of $R^1$, $R^2$ and $R^3$ are not alkyl, aryl or hydroxyl;

$L_1$ is alkyldiyl, heteroalkyldiyl, aryldiyl or heteroaryldiyl;

Y is —$C(O)N(R^4)(R^5)$, —$N(R^4)C(O)R^7$, —$N(R^4)S(O_2)R^7$, —$S(O)_2N(R^4)(R^5)$, —$OC(O)R^7$, —$OC(O)N(R^4)(R^5)$, —$N(R^4)C(O)OR^7$, —$N(R^4)C(O)N(R^5)(R^6)$ or —$N(R^4)S(O_2)N(R^5)(R^6)$; and $R^4$, $R^5$ and $R^6$ are independently hydrogen, ($C_1$-$C_6$) alkyl optionally substituted with one or more hydroxy or cyano groups or ($C_5$-$C_7$) aryl optionally substituted with one or more hydroxy or cyano groups;

$R^7$ is ($C_1$-$C_6$) alkyl optionally substituted with one or more hydroxy or cyano groups or ($C_5$-$C_7$) aryl optionally substituted with one or more hydroxy or cyano groups; and $R^{14}$ is ($C_1$-$C_6$) alkyl;

provided that one of $R^4$, $R^5$ or $R^6$ is not hydrogen.

In another aspect, a composition including a compound of Formula (II) covalently bonded to a substrate is provided. In some embodiments, the composition is in a flow-through bed suitable for use a reverse phase chromatographic medium.

In still another aspect, a composition comprising the compound of structural Formula (II) covalently bonded to a substrate and a compound of structural Formula (IV) covalently bonded to the substrate is provided wherein:

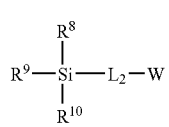

(IV)

$R^8$, $R^9$, and $R^{10}$ are independently alkyl, alkoxy, alkoxycarbonyl, alkylsulfonyloxy, amino aryl, aryloxycarbonyl, aryloxy, arylsulfonyloxy, halo or hydroxyl optionally substituted with one or more of the same or different $R^{14}$ groups, provided that at least one of $R^1$, $R^2$ and $R^3$ are not alkyl, aryl or hydroxyl;

$R^{15}$ is $(C_1-C_6)$ alkyl;

$L_2$ is alkyldiyl, heteroalkyldiyl, aryldiyl or heteroaryldiyl; and

W is an ionizable group.

In still another aspect, a chromatographic method is provided. An aqueous liquid is flowed through a bed of separation medium, which includes either a composition containing a compound of Formula (II) covalently bonded to a substrate or a composition comprising the compound of structural Formula (II) covalently bonded to a substrate and a compound of structural Formula (IV) covalently bonded to the substrate.

In still another aspect, a method for chromatographic separation of analytes in a liquid sample is provided. The liquid sample is flowed through medium, which includes a composition containing a compound of Formula (II) covalently bonded to a substrate or a composition comprising the compound of structural Formula (II) covalently bonded to a substrate and a compound of structural Formula (IV) covalently bonded to the substrate.

In still another aspect, a method for simultaneous analysis of inorganic analytes and organic analytes in a liquid sample is provided. The liquid sample is flowed through medium, which includes a composition containing a compound of Formula (II) covalently bonded to a substrate or a composition of a compound of structural Formula (II) and a compound of structural Formula (IV) covalently bonded to a substrate.

4. BRIEF DESCRIPTION OF THE DRAWINGS

5. DETAILED DESCRIPTION 5.1 Definitions

Figure 1:
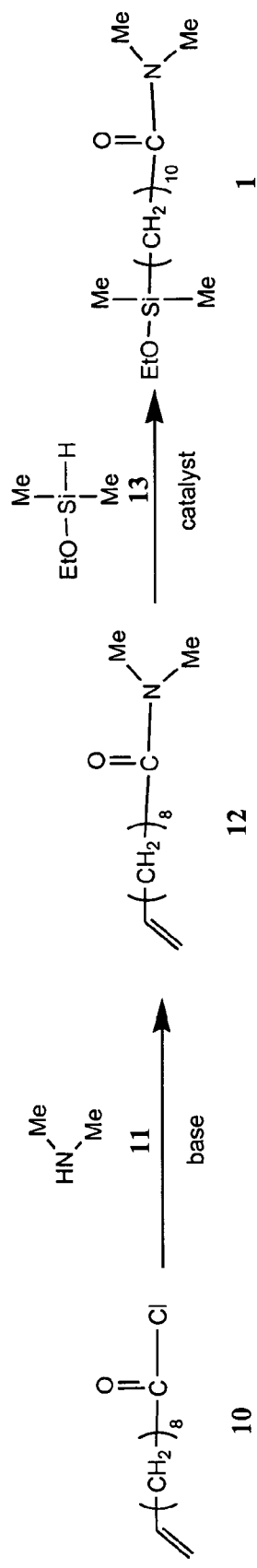
FIG. 1 illustrates the synthesis of an amide of Formula (II)

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms. In other embodiments, an alkyl group comprises from 1 to 10 carbon atoms.

"Alkanyl" by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl (t-butyl), cyclobutan-1-yl, etc.; and the like.

"Alkenyl" by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl, cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent, refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent, refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc. butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is ($C_1$-$C_{20}$) alkyldiyl. In other embodiments, the alkyldiyl group is ($C_1$-$C_{10}$) alkyldiyl. In still other embodiments, the alkyldiyl group is a saturated acyclic alkanyldiyl group in which the radical centers are at the terminal carbons, e.g., methandiyl(methano); ethan-1,2-diyl(ethano); propan-1,3-diyl (propano); butan-1,4-diyl(butano); and the like (also referred to as alkyleno, defined infra).

"Alkyleno" by itself or as part of another substituent, refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In some embodiments, the alkyleno group is ($C_1$-$C_{20}$) alkyleno. In other embodiments, the alkyleno group is ($C_1$-$C_{10}$) alkyleno. In still other embodiments, the alkyleno group is a straight-chain saturated alkano groups, e.g., methano, ethano, propano, butano, and the like.

"Alkylsulfonyloxy" by itself or as part of another substituent, refers to a radical —OS(O)$_2$R$^{30}$ where R$^{30}$ represents an alkyl or cycloalkyl group as defined herein.

"Alkoxy" by itself or as part of another substituent, refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent, refers to a radical —C(O)OR$^{32}$ where R$^{32}$ represents an alkyl or cycloalkyl group as defined herein.

"Aryl" by itself or as part of another substituent, refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 5 to 20 carbon atoms. In other embodiments, an aryl group comprises from 5 to 12 carbon atoms.

"Aryldiyl" by itself or as part of another substituent refers to a divalent hydrocarbon radical derived by the removal of one hydrogen atom from each of two different carbon atoms of a parent aromatic system or by removal of two hydrogen atoms from a single carbon atom of a parent aromatic ring system. The two monovalent radical centers or each valency of the divalent center can form bonds with the same or different atom(s). Typical aryldiyl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryldiyl group comprises from 5 to 20 carbon atoms. In other embodiments, an aryldiyl group comprises from 5 to 12 carbon atoms.

"Aryloxycarbonyl" by itself or as part of another substituent, refers to a radical —C(O)OR$^{33}$ where R$^{33}$ represents an aryl group as defined herein.

"Arylsulfonyloxy" by itself or as part of another substituent, refers to a radical —OS(O)$_2$R$^{35}$ where R$^{35}$ represents an alkyl or cycloalkyl group as defined herein.

"Cycloalkyl" by itself or as part of another substituent, refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In some embodiments, the cycloalkyl group is ($C_3$-$C_{10}$) cycloalkyl. In other embodiments, the cycloalkyl group is ($C_3$-$C_7$) cycloalkyl.

"Heteroalkyl, Heteroalkanyl, Heteroalkenyl, Heteroalkanyl, Heteroalkyldiyl and Heteroalkyleno" by themselves or as part of another substituent, refer to alkyl, alkanyl, alkenyl, alkynyl, alkyldiyl and alkyleno groups, respectively, in which one or more of the carbon atoms (and any associated hydrogen atoms) are each independently replaced with the same or different heteroatomic groups. Typical heteroatomic groups which can be included in these groups include, but are not limited to, —O—, —S—, —O—O—, —S—S—, —O—S—, —NR$^{35}$R$^{36}$—, =N—N=, —N=N—, —N=N—NR$^{37}$R$^{38}$, —PR$^{39}$—, —P(O)$_2$—, —PR$^{40}$—, —O—P(O)$_2$—, —SO—, —SO$_2$—, —SnR$^{41}$R$^{42}$— and the like, where R$^{35}$, R$^{36}$, R$^{37}$, R$^{38}$, R$^{39}$, R$^{40}$, R$^{41}$ and R$^{42}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is from 5-20 membered heteroaryl. In other embodiments, the heteroaryl group is from 5-10 membered heteroaryl. In still other embodiments, the heteroaryl groups are those derived from thiophene, pyrrole, benzothiophene, benzofuran, indole, pyridine, quinoline, imidazole, oxazole and pyrazine.

"Heteroaryldiyl" by itself or as part of another substituent refers to a divalent radical derived by the removal of one hydrogen atom from each of two different carbon atoms of a parent heteroaromatic system or by removal of two hydrogen atoms from a single carbon atom of a parent aromatic ring system. The two monovalent radical centers or each valency of the divalent center can form bonds with the same or different atom(s). Typical heteroaryldiyl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, a heteroaryldiyl group comprises from 5 to 20 carbon atoms. In other embodiments, a heteroaryldiyl group comprises from 5 to 12 carbon atoms.

"Parent Aromatic Ring System" by itself or as part of another substituent, refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" by itself or as part of another substituent, refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Substituted" refers to a group in which one or more hydrogen atoms are independently replaced with the same or different substituent(s). Typical substituents include, but are not limited to, —M, —$R^{60}$, —$O^-$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —$S(O)_2OH$, —$S(O)_2R^{60}$, —$OS(O_2)O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include —M, —$R^{60}$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$, more preferably, —M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$, most preferably, —M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, $C(O)OR^{60}$, —$C(O)O^-$, where $R^{60}$, $R^{61}$ and $R^{62}$ are as defined above.

5.2 Organosilanes and Substrates Thereof

The present invention provides novel silane compounds which have both hydrophobic and ionic functionality. At one terminus of the novel silane compound is a silyl group, which can be covalently attached to a substrate. At the other end of the novel silane compound is a short head chain (e.g., ($C_1$-$C_6$) alkyl). The silyl group and the short head chain are connected via a linker joined to a polar group. The linkers may be alkyl, aryl, heteroaryl or heteroalkyl groups while the polar group may be amide, carbamate, urea, sulfonamide, etc.

In one aspect, a compound described by Formula (I) is provided

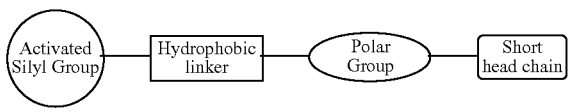

I or salts, solvates or hydrates thereof. Compounds of Formula (I) have at least one activated silyl group, a head chain joined by a linker connected to a polar group.

An "activated silyl group" refers to silicon moieties, which are capable of reacting with the surface of a substrate to form a covalent bond with the surface. For example, an activated silyl group can react with the surface of a silica substrate comprising surface Si—OH groups to create siloxane bonds between compounds of Formula (I) and the substrate. Exemplary activated silyl groups include, but are not limited to, —Si(OMe)$_3$, —SiMe(OMe)$_2$, —SiMe$_2$(OMe), —Si(OEt)$_3$, —SiMe(OEt)$_2$, —SiMe$_2$(OEt), —SiMe$_2$NMe$_2$ and —SiCl$_3$. A "linker" refers to an alkyl, heteroalkyl, aryl or heteroaryl group. A "polar group" refers to an amide, sulfonamide, carbamate, urea, ester, etc. The linker in compounds of Formula (I) serve as a spacer between the activated silyl group and the polar group.

In some embodiments, a compound of structural Formula (II) is provided:

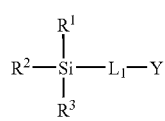

(II)

or salts, solvates or hydrates thereof
wherein:
$R^1$, $R^2$ and $R^3$ are independently alkyl, alkoxy, alkoxycarbonyl, alkylsulfonyloxy, amino, aryl, aryloxycarbonyl, arylsulfonyloxy, halo or hydroxyl, optionally substituted with one or more $R^{14}$ groups, provided that at least one of $R^1$, $R^2$ and $R^3$ are not alkyl, aryl or hydroxyl;

$L_1$ is alkyldiyl, heteroalkyldiyl, aryldiyl or heteroaryldiyl;

Y is —C(O)N($R^4$)($R^5$), —N($R^4$)C(O)$R^7$, —N($R^4$)S(O$_2$)$R^7$, —S(O)$_2$N($R^4$)($R^5$), —OC(O)$R^7$, —OC(O)N($R^4$)($R^5$), —N($R^4$)C(O)O$R^7$, —N($R^4$)C(O)N($R^5$)($R^6$) or —N($R^4$)S(O$_2$)N($R^5$)($R^6$); and $R^4$, $R^5$ and $R^6$ are independently hydrogen, ($C_1$-$C_6$) alkyl optionally substituted with one or more hydroxy or cyano groups or ($C_5$-$C_7$) aryl optionally substituted with one or more hydroxy or cyano groups;

$R^7$ is ($C_1$-$C_6$) alkyl optionally substituted with one or more hydroxy or cyano groups or ($C_5$-$C_7$) aryl optionally substituted with one or more hydroxy or cyano groups and $R^{14}$ is ($C_1$-$C_6$) alkyl;
provided that one of $R^4$, $R^5$ or $R^6$ is not hydrogen.

In some embodiments, $R^1$, $R^2$ and $R^3$ are independently alkyl, alkoxy or halo. In other embodiments, $R^1$, $R^2$ and $R^3$ are alkoxy. In still other embodiments, $R^1$, $R^2$ and $R^3$ are alkyl or alkoxy. In still other embodiments, $R^1$, $R^2$ and $R^3$ are ethoxy or methyl.

In some embodiments, $L_1$ is alkyldiyl. In other embodiments, $L_1$ is alkanyldiyl. In still other embodiments, $L_1$ is alkanyleno. In still other embodiments, $L_1$ is ($C_6$-$C_{20}$) alkanyleno. In still other embodiments, $L_1$ is ($C_8$-$C_{15}$) alkanyleno. In still other embodiments, $L_1$ is ($C_{10}$-$C_{11}$) alkanyleno.

In some embodiments, $R^4$, $R^5$ and $R^6$ are independently hydrogen, alkyl, or aryl. In other embodiments, $R^4$, $R^5$ and $R^6$ are independently alkyl, or aryl. In still other embodiments, $R^4$, $R^5$ and $R^6$ are independently methyl or phenyl. In still other embodiments, $R^4$, $R^5$ and $R^6$ are methyl.

In some embodiments, $R^1$, $R^2$ and $R^3$ are independently alkyl, alkoxy or halo, $L_1$ is alkyldiyl and $R^4$, $R^5$ and $R^6$ are independently hydrogen, alkyl, or aryl. In other embodiments, $R^1$, $R^2$ and $R^3$ are alkyl or alkoxy, $L_1$ is ($C_8$-$C_{15}$) alkanyleno and $R^4$, $R^5$ and $R^6$ are independently alkyl, or aryl. In still other embodiments, $R^1$, $R^2$ and $R^3$ are ethoxy or methyl, $L_1$ is ($C_{10}$-$C_{11}$) alkanyleno and $R^4$, $R^5$ and $R^6$ are independently methyl or phenyl.

In some embodiments, $R^4$, $R^5$ and $R^6$ are methyl. In other embodiments, $R^5$ is phenyl.

In some embodiments, the compounds of Formula (II) have the structure:

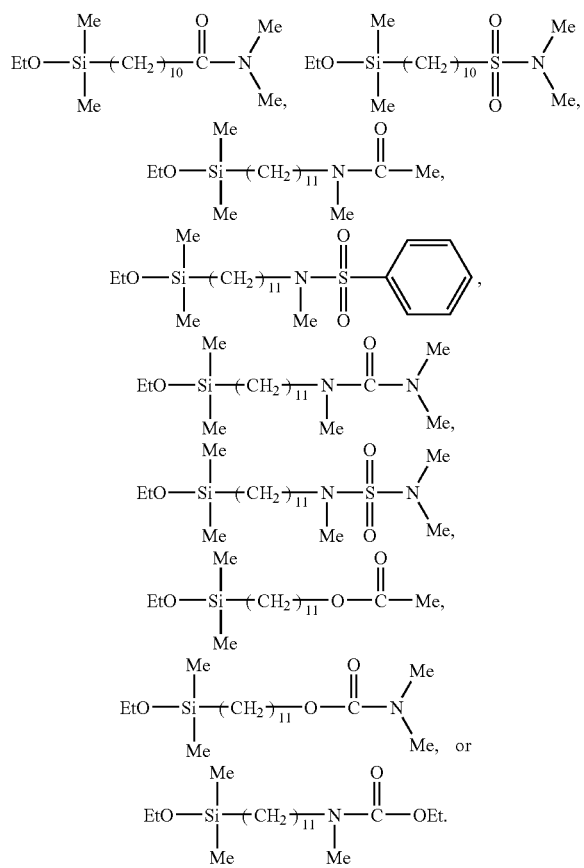

Exemplary methods of synthesizing compounds described herein are presented in Schemes 1-4, infra. Starting materials useful for preparing compounds described herein are commercially available or can be prepared by well-known synthetic methods. Other methods for synthesis of the compounds described herein will be readily apparent to the skilled artisan. Accordingly, the methods presented in Schemes 1-4 herein are illustrative rather than comprehensive.

Referring now to FIG. 1, 10-undecanoyl chloride 10 is reacted with dimethylamine 11 to provide amide 12. Amide 12 is then hydrosilylated with silane 13 in presence of a platinum catalyst to yield compound 1.

Figure 2:
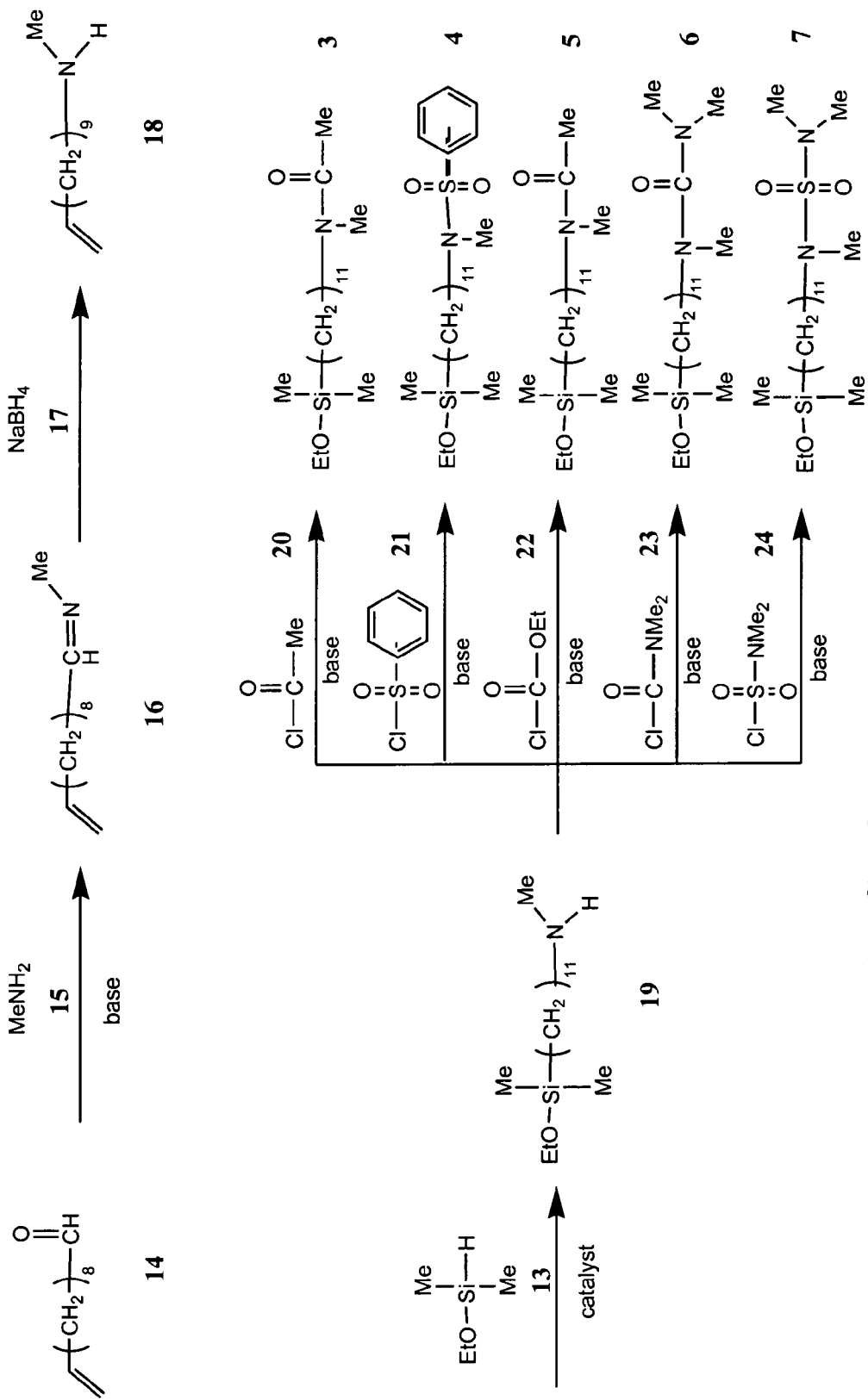
FIG. 2 illustrates the synthesis of amine derivatives of Formula (II)

Referring now to FIG. 2, the imine of undecylenic aldehyde 14 is formed upon treatment with methylamine 15. The imine 16 is reduced with sodium borohydride 17 to provide amine 18 which is hydrosilylated with silane 13 in the presence of a platinum catalyst to provide the mono-methylated amine 19. Amine 19 may be reacted with acetyl chloride 20, benzenesulfonyl chloride 21, ethyl chloroformate 22, N,N-dimethylcarbamyl chloride 23 or N,N-dimethylsulphamoyl chloride 24 to provide silicon compounds 3, 4, 5, 6 and 7, respectively.

Figure 3:
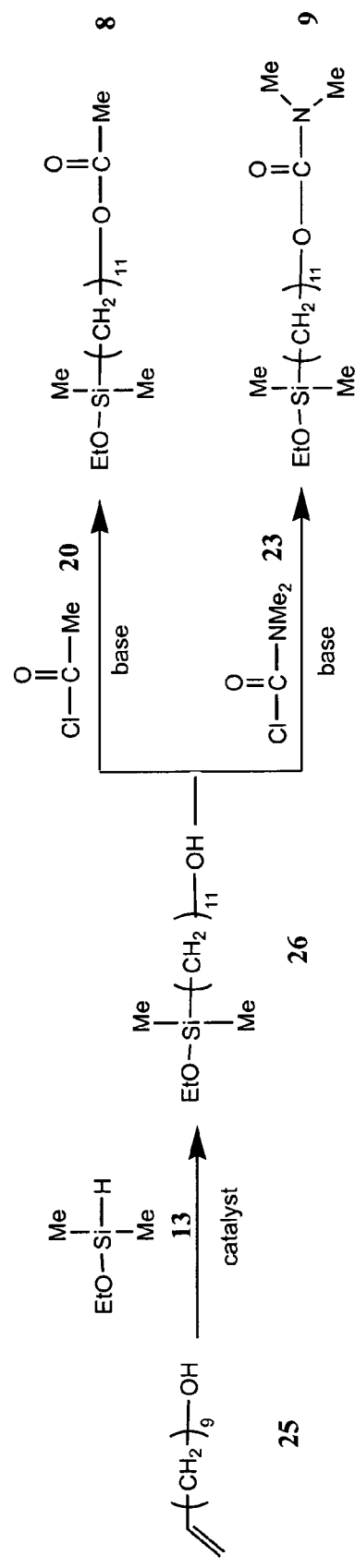
FIG. 3 illustrates the synthesis of alcohol derivatives of Formula (II)

Referring now to FIG. 3, 10-undecen-1-ol 25 is hydrosilylated with silane 13 in the presence of a platinum catalyst to provide silyl alcohol 26. Acylation of silyl alcohol 26 with acetyl chloride 20 or N,N-dimethylcarbamyl chloride 23, provides silicon compounds 8 and 9, respectively.

Figure 4:
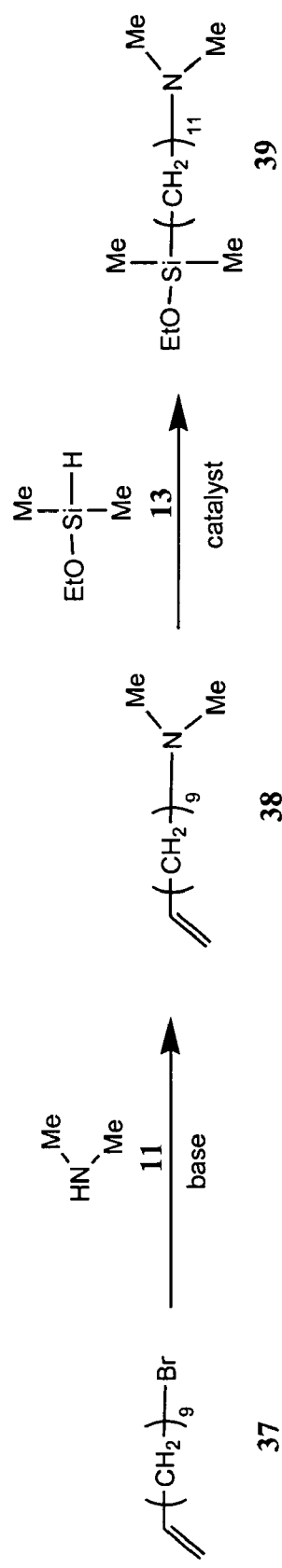
FIG. 4 illustrates synthesis of a compound of Formula (IV)
Figure 5:
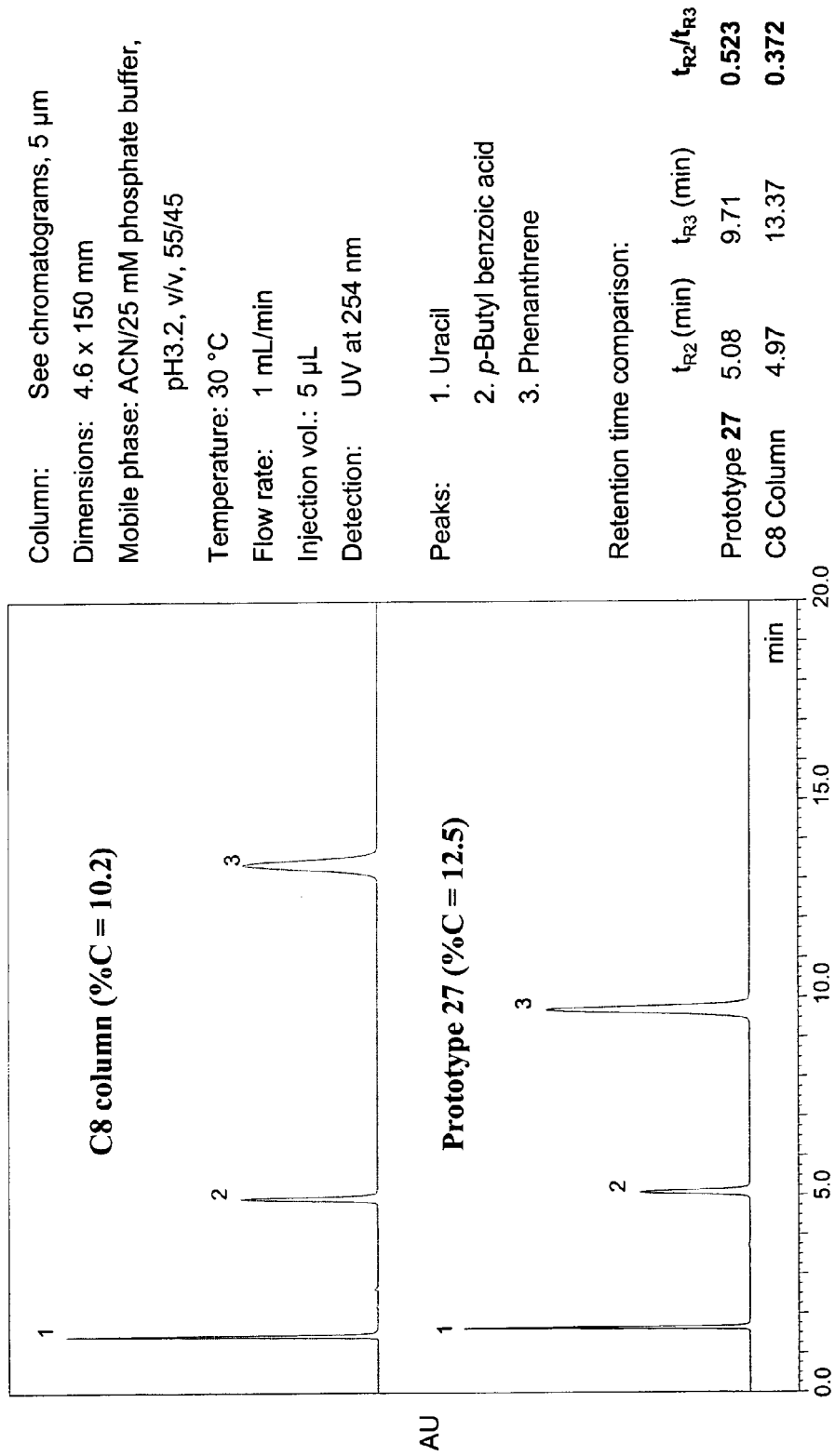
FIG. 5 illustrates the separation of uracil, p-butyl benzoic acid and phenanthrene by a C8 column and a column packed with composition 27.

Referring now to FIG. 4, bromide 37 is displaced with dimethylamine 11 to provide the amine 38 which is then hydrosilated with silane in the presence of platinum catalyst to yield the silylamine 39. Compound 39 may be used as the ionizable component of a mixed mode chromatography support.

Those of skill in the art will appreciate that the synthetic strategies disclosed, supra, may be readily adapted to make silanes with aryl, heteroaryl and heteroalkyl linkers by varying the starting amine or acyl chloride or alkyl halide. Further, diverse methods are known to those of skill in the art to accomplish the transformations above (or equivalents thereof) and may be found in any compendia of organic synthesis (see e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; and Paquette, "Encyclopedia of Reagents for Organic Synthesis," John Wiley & Sons, 1995).

The compounds disclosed, supra, may be reacted with substrates to form functionalized substrates, which can be used in a wide range of different applications. The compounds disclosed, supra, incorporate both hydrophobic and polar sites in one molecular structure and have reproducible surface chemistries in reactions with substrate surfaces.

In some embodiments, a compound of structural Formula (II) is covalently bonded to a substrate. In other embodiments, the compound of structural Formula (II) is covalently bonded to the substrate by reaction of one or more of $R^1$, $R^2$ and $R^3$ groups with reactive groups on the substrate such, for example, silanol, alkoxysilane, halosilane or aminosilane.

In some embodiments, a compound of structural Formula (II) is covalently bonded through the $SiR^1(R^2)(R^3)$ group, to another compound of structural Formula (II) by reaction with reactive groups selected from the group consisting of silanol, alkoxysilane or halosilane on the other compound. In this embodiment, the two compounds are both covalently bonded to the substrate.

In some embodiments, compositions of structural Formula (III) are provided

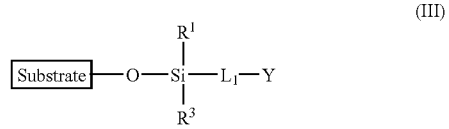

(III)

where $R^1$, $R^3$, L and Y are as defined, supra.

In other embodiments, compositions having the following structures are provided:

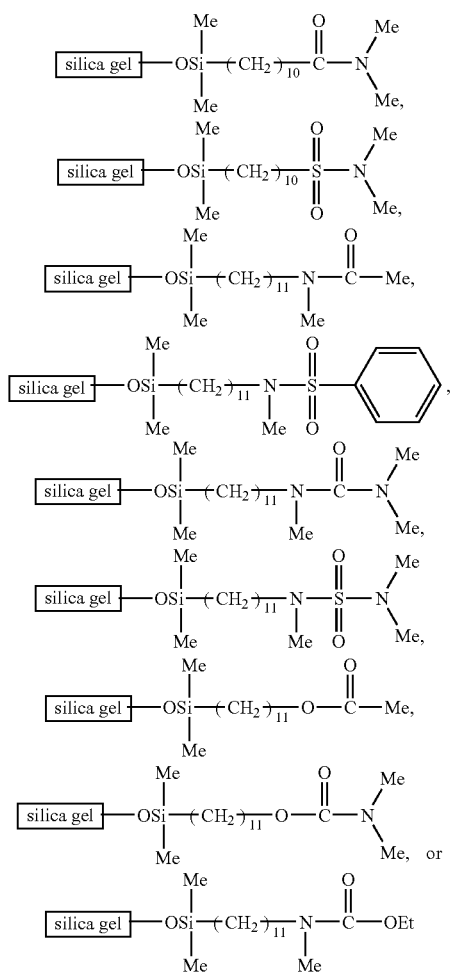

In still other embodiments, compositions of at least one compound of structural Formula (II) and at least one compound of structural Formula (IV) covalently bonded to a substrate are provided where

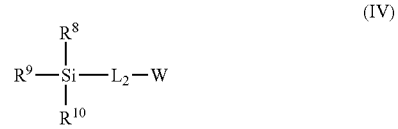

(IV)

$R^8$, $R^9$, and $R^{10}$ are independently alkyl, alkoxy, alkoxycarbonyl, alkylsulfonyloxy, amino aryl, aryloxycarbonyl, aryloxy, arylsulfonyloxy, halo or hydroxyl optionally substituted with one or more of the same or different $R^{15}$ groups, provided that at least one of $R^1$, $R^2$ and $R^3$ are not alkyl, aryl or hydroxyl;

$R^{15}$ is $(C_1\text{-}C_6)$ alkyl;

$L_2$ is alkyldiyl, heteroalkyldiyl, aryldiyl or heteroaryldiyl; and

W is an ionizable group.

In other embodiments, a composition of structural Formula (V) is provided

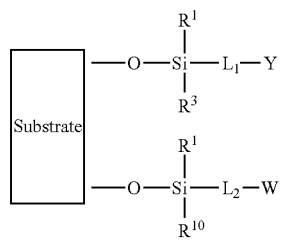

(V)

where $R^1$, $R^3$, $L_1$, $L_2$, Y and W are as defined, supra.

In some embodiments, $R^8$, $R^9$ and $R^{10}$ are independently alkyl, alkoxy or halo. In other embodiments, $R^8$, $R^9$ and $R^{10}$ are alkoxy. In still other embodiments, $R^8$, $R^9$ and $R^{10}$ are alkyl or alkoxy. In still other embodiments, $R^8$, $R^9$ and $R^{10}$ are ethoxy or methyl.

In some embodiments, $L_2$ is alkydiyl. In other embodiments, $L_2$ is alkanyldiyl. In still other embodiments, $L_2$ is alkyleno. In still other embodiments, $L_2$ is $(C_6\text{-}C_{20})$ alkanyleno. In still other embodiments, $L_2$ is $(C_8\text{-}C_{15})$ alkanyleno. In still other embodiments, $L_2$ is $(C_{10}\text{-}C_{11})$ alkanyleno.

In some embodiments, W is $-CO_2^-$, $-SO_3^-$, $-P(O)(OR^{11})O-$, $-NR^{11}R^{12}$, or $-N^+R^{11}R^{12}R^{13}$, where $R^{11}$, $R^{12}$, $R^{13}$ are independently hydrogen or $(C_1\text{-}C_6)$ alkyl. In other embodiments, W is $-NR^{11}R^{12}$, or $-N^+R^{11}R^{12}R^{13}$ wherein $R^{11}$, $R^{12}$ and $R^{13}$ are methyl.

In some embodiments, $R^1$, $R^2$, $R^3$, $R^8$, $R^9$ and $R^{10}$ are independently alkyl, alkoxy or halo, $L_1$ and $L_2$ are alkyldiyl, $R^4$, $R^5$ and $R^6$ are independently hydrogen, alkyl, or aryl and W is $-NR^{11}R^{12}$, or $-N^+R^{11}R^{12}R^{13}$ where $R^{11}$, $R^{12}$ and $R^{13}$ are independently $(C_1\text{-}C_6)$ alkyl.

In some embodiments, $R^1$, $R^2$, $R^3$, $R^8$, $R^9$ and $R^{10}$ are alkyl or alkoxy, $L_1$ and $L_2$ are $(C_8\text{-}C_{15})$ alkanyleno, $R^4$, $R^5$ and $R^6$ are independently alkyl, or aryl and W is $-NR^{11}R^{12}$, or $-N^+R^{11}R^{12}R^{13}$ where $R^{11}$, $R^{12}$ and $R^{13}$ are independently $(C_1\text{-}C_6)$ alkyl. In other embodiments, $R^1$, $R^2$, $R^3$, $R^8$, $R^9$ and $R^{10}$ are ethoxy or methyl, $L_1$ and $L_2$ are $(C_{10}\text{-}C_{11})$ alkanyleno, $R^4$, $R^5$ and $R^6$ are independently methyl or phenyl and W is $-NR^{11}R^{12}$, or $-N^+R^{11}R^{12}R^{13}$ where $R^{11}$, $R^{12}$ and $R^{13}$ are methyl. In a more specific embodiment, $R^4$, $R^5$ and $R^6$ are methyl. In another more specific embodiment, $R^5$ is phenyl.

In some embodiments, a compound of Formula (II) and the compound of Formula (IV) are covalently bonded to the substrate by reaction of one or more of $R^1$, $R^2$ and $R^3$ and one or more of $R^8$, $R^9$ and $R^{10}$ with reactive groups on the substrate selected from the group consisting of silanol, alkoxysilane, halosilane or aminosilane. In other embodiments, $R^2$ and $R^9$ are $-OEt$. In still other embodiments, a composition where the compound of Formula (II) is

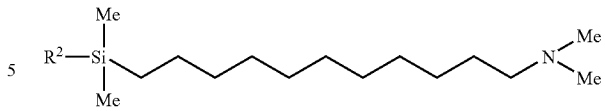

and the compound of Formula (IV) is

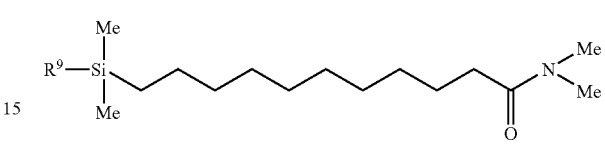

is provided.

In still other embodiments a composition of the following structure is provided:

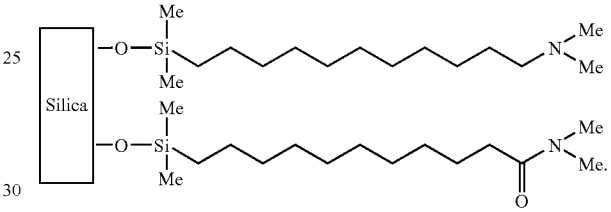

In some embodiments, compounds of Formulae (I) and (II) are covalently attached to substrates as shown, supra. In these embodiments, the polar group is disposed from the surface of the substrate, which may improve hydrolytic stability of the functionalized substrate. Compounds of Formulae (I) and (II) can be attached to substrates (e.g., silica) to provide a functionalized stationary phase for various chromatographic separations such as reversed phase separations of surfactants. Further, compounds of Formulae (I) and (II) may be mixed with silyl ligands containing one or more ion exchange functionality (e.g., compounds of Formula (IV) prior to reaction with the substrate to provide mixed mode substrates of varying selectivity that also can be used for reversed phase separations of surfactants.

Compounds of Formulae (I), (II) and (IV) may be covalently bound to a substrate by reaction of $R_1$, $R_2$ or $R_3$ of the Si functionality with reactive groups on the substrate selected from the group consisting of silanol, alkoxysilane, halosilane and aminosilane moieties. In some embodiments, compounds of Formulae (I), (II) and (IV) which are covalently bonded to a substrate may be cross linked to one or more compounds of Formulae (I), (II) or (IV) by reaction with reactive groups selected from the group consisting of silanol, alkoxysilane or halosilane on other compound of Formulae (I), (II) or (IV).

Compounds of Formulae (I), (II) and (IV) can be covalently attached to a variety of substrates. Exemplary substrates include materials that have a functional group that can react with activated silyl groups in compounds of Formulae (I), (II) and (IV). Thus, compounds of Formulae (I), (II) and (IV) can be attached, for example, to silica based materials such as glass surfaces, or the surfaces of other silicon oxide, titanium oxide, germanium oxide, zirconium oxide and aluminum oxide based materials; and also to the surfaces of various carbonized materials, metals, crosslinked and noncrosslinked polymers, which contain suitable functional groups for reacting with activated silyl groups. Examples of suitable functional groups include silanols, alkoxysilanes, titanium hydroxides, zirconium hydroxides, etc. Compounds of Formulae (I), (II) and (IV) can also be incorporated into polymeric or sol-gel networks by utilizing reactive silicon functionalities. Compounds of Formulae (I), (II) and (IV) containing polymerizable groups or groups that can be converted into radicals and/or ion-radicals and/or ions, can be used for making polymeric materials and for surface grafting, by utilizing those groups and/or reactive silicon functionalities. The resulting materials can be applied for a development of adsorbents, membranes, filters, microfluidic devices, microchips, and functionalized surfaces for various types of separation, detection, and analysis.

In some embodiments, mono- and multi-layered surfaces are prepared by treating silica substrates with compounds of Formulae (I), (II) and/or (IV). Compounds of Formulae (I), (II) and/or (IV) can be covalently attached to a variety of substrates, such as silica gel, zirconia, hybrid sol-gel/polymers or glass plates. Suitable silica gels comprise non-porous, or porous silica particles of different pore sizes, preferably from 20 Å to 3000 Å and more preferably, from 60 Å to 2000 Å; and of different particle sizes, preferably, from 0.2 um to 1000 um, and more preferably, from 2 um to 50 um. The attachment reaction can be carried out in a slurry of silica gel in an inert solvent, such as toluene, at elevated temperature. Water, acid or base catalyst can be applied to enhance the surface coverage, depending on the type of properties desired for the separation media.

Alternatively, an aminosilane compound, such as bis(trimethoxysilylpropyl)amine can be used for modifying underivatized silica gel by incorporating the reactive amino group onto a surface. Then, a reagent, such as acyl chloride, carbamyl chloride, sulfonyl chloride, or isocyanate, containing a proper functional group, can be reacted with the aminated silica gel to form the corresponding bonded phase.

The compositions described herein may be used as packing for chromatography columns. The packing may be particles, monoliths (i.e., material containing pores) or packed bed resins which are loaded into a housing suitable for a chromatography column.

Also provided is a packing of a compound of structural Formula (I) covalently bonded to a substrate and a compound of structural Formula (IV) bonded to another substrate. In some embodiments, the substrates are silica substrates.

The compositions described herein may be used to resolve a variety of compounds. Generally, the compositions described herein may be used to separate surfactants. The compositions described herein may also be used, in some situations to resolve a mixture including cationic surfactants, anionic surfactants and neutral surfactants in a single chromatographic run.

This invention provides simple and versatile approaches to produce a variety of novel solid supports with excellent hydrolytic stability. The method of synthesis allows for efficient incorporation of different functionalities onto the surfaces of the substrates and silica substrates, in particular. The resulting materials can be applied for development of adsorbents, membranes, filters, microfluidic devices, microchips, and functionalized surfaces for various types of separation, detection and analysis.

6. EXAMPLES

The following examples are provided by way of illustration only and not by way of limitation. Those of skill in the art will readily recognize a variety of noncritical parameters that could be changed or modified to yield essentially similar results.

6.1 Preparation of Compound 1

Dimethylamine was mixed with an excess of triethylamine (2.0 eq.) in anhydrous $CH_2Cl_2$ and kept at between about 0° C. and about 5° C. for 20 min. Then, a solution of 10-undecenoyl chloride (1.0 eq.) in $CH_2Cl_2$ was added dropwise and the mixture was stirred at ambient temperature for 12 h. The reaction mixture was washed with water, dried over $Na_2SO_4$ and the solvent was removed in vacuo to yield the dimethylamide of 10-undecenoic acid. Excess dimethylethoxysilane (10 eq.) was added to the amide followed by addition of a solution of catalyst (0.1 mol %), (e.g., hexachloroplatinic acid in a minimum amount of ethanol). After stirring at 50° C. for 24 h, the silane and solvent were removed in vacuo to provide compound 1.

6.2 Example 2

Preparation of Compounds 3, 4, 5, 6 and 7

To a solution of 10-undecylenic aldehyde (1 eq.) in anhydrous methanol was added excess methylamine in anhydrous methanol (3 eq.). After 6 h at ambient temperature, the reaction mixture was filtered followed by concentration in vacuo to give imine 16.

Then imine 16 was reduced with sodium borohydride (6 eq.) in methanol at ambient temperature for 24 h. After removal of all volatiles in vacuo, amine 18 was obtained by partitioning the residue between $Et_2O$ and $H_2O$, drying over $Na_2SO_4$ and concentrating in vacuo.

Then excess dimethylethoxysilane (10 eq.) was added to compound 18 followed by addition of a solution of catalyst (0.1 mol %), (e.g., hexachloroplatinic acid in a minimum amount of ethanol). After stirring at 50° C. for 24 h, the silane and solvent were removed in vacuo to provide silyl compound 19.

Compound 19 was mixed with excess triethylamine (2.0 eq.) in anhydrous $CH_2Cl_2$ and kept at between about 0° C. and about 5° C. for 20 min. A solution of acetyl chloride (1.2 equiv) in anhydrous $CH_2Cl_2$ was then added dropwise and the mixture was stirred at ambient temperature for 12 h. All volatiles were removed in vacuo and hexanes were added to precipitate triethylammonium chloride salt. Compound 3 was obtained after filtration and removal of solvent in vacuo.

Similarly, compounds 4, 5, 6 and 7 can be prepared by reacting compound 19 with sulfonyl chloride, ethyl chloroformate, N,N-dimethylcarbamyl chloride and N, N-dimethylsulphamoyl chloride, respectively.

6.3 Example 3

Preparation of Compounds 8 and 9

Excess dimethylethoxysilane (10 equiv) was added to 10-undecen-1-ol (25) followed by addition of a solution of catalyst (0.1 mol %), (e.g., hexachloroplatinic acid in a minimum amount of ethanol). After stirring at 50° C. for 24 h, the silane and solvent were removed in vacuo to provide silyl compound 26.

Compound 26 was then mixed with excess triethylamine (2.0 eq.) in anhydrous $CH_2Cl_2$ and kept at between about 0° C. and about 5° C. for 20 min. Then, a solution of acetyl chloride (1.2 eq.) in anhydrous $CH_2Cl_2$ was added dropwise and the mixture stirred at ambient temperature for 12 h. All volatiles were removed in vacuo and hexanes were added to precipitate triethylammonium chloride salt. Compound 8 was obtained after filtration and concentration in vacuo.

Similarly compound 9 can be prepared by reacting compound 26 with N, N-dimethylcarbamyl chloride.

6.4 Example 4

Preparation of Compound 39

A 5° C. solution of 11-bromo-1-undecene in THF was added dropwise to a solution of dimethylamine (10 eq.) in THF and stirred at ambient temperature for 12 h. The volatiles were removed in vacuo and the residue was partitioned between $CH_2Cl_2$ and $H_2O$, dried over $Na_2SO_4$ followed by removal of solvent in vacuo to provide 38.

Excess dimethylethoxysilane (10 eq.) was added to compound 38 followed by addition of a solution of catalyst (0.1 mol %), (e.g., hexachloroplatinic acid in a minimum amount of ethanol). After stirring at 50° C. for 24 h, the silane and solvent were removed in vacuo to provide silyl compound 39.

6.5 Example 5

Synthesis of Compositions 27, 28, 29, 30, 31, 32, 33, 34 and 35

Compounds 27, 28, 29, 30, 31, 32, 33, 34, or 35 in an inert solvent (e.g., toluene at elevated temperature) were reacted with a slurry of selected raw silica gel with the following physical properties: average particle size, 5.0 µm; specific surface area, 300 m²/g; mean pore size, 120 Å; pore volume, 1.00 mL/g. The addition of water, acid or base catalyst can be applied to control the surface coverage. After a certain period of time (from 3 h to 6 days), the reaction slurry was filtered, washed with acetone, and dried in vacuum oven at 50° C. for 5 h. A proper end-capping reagent, such as a trialkylsilyl chloride, may also be required to produce a packing material for chromatographic separations.

6.6 Example 6

Synthesis of Composition 36

Compounds 27 and 39 were mixed in appropriate ratios in an inert solvent such as toluene at elevated temperature. Then raw silica with the characteristics described in Example 6 was added to the above mixture to form a reaction slurry which was kept elevated temperature for 3 days. The reaction slurry was filtered, washed with acetone, and dried in vacuum oven at 50° C. for 5 h to give functionalized silica of composition 36. A proper end-capping reagent, such as a trialkylsilyl chloride, may also be required to produce a packing material for the reversed-phase chromatographic separation.

6.7 Example 7

Polarity Test

HPLC chromatography of a test mixture containing uracil, p-butyl benzoic acid and phenanthrene on composition 27 packed into 4.6×150 mm stainless steel tubes using traditional high pressure slurry techniques yielded the results illustrated in FIG. 1. The mixture (injection volume of about 5 µL) was eluted with $CH_3CN$/25 mM phosphate buffer at about pH 3.2 at a flow rate of about 1 mL/min at about 30° C.

and was detected at 210 nm. For comparison, a C8 column of the same column dimension and prepared using the same silica substrate was also used in chromatography of the test mixture.

FIG. 1 illustrates the high polarity of composition 27, since the relative retention of the polar compound p-butyl benzoic acid to neutral compound phenanthrene is higher on composition 27 than that on C8 column despite that fact that the latter has lower carbon content. Enhancement of polarity may be due to the placement of polar group at the end of the ligand furthest disposed from the silica surface.

6.8 Example 8

Separation of Cationic, Nonionic and Anionic Surfactants

Figure 6:
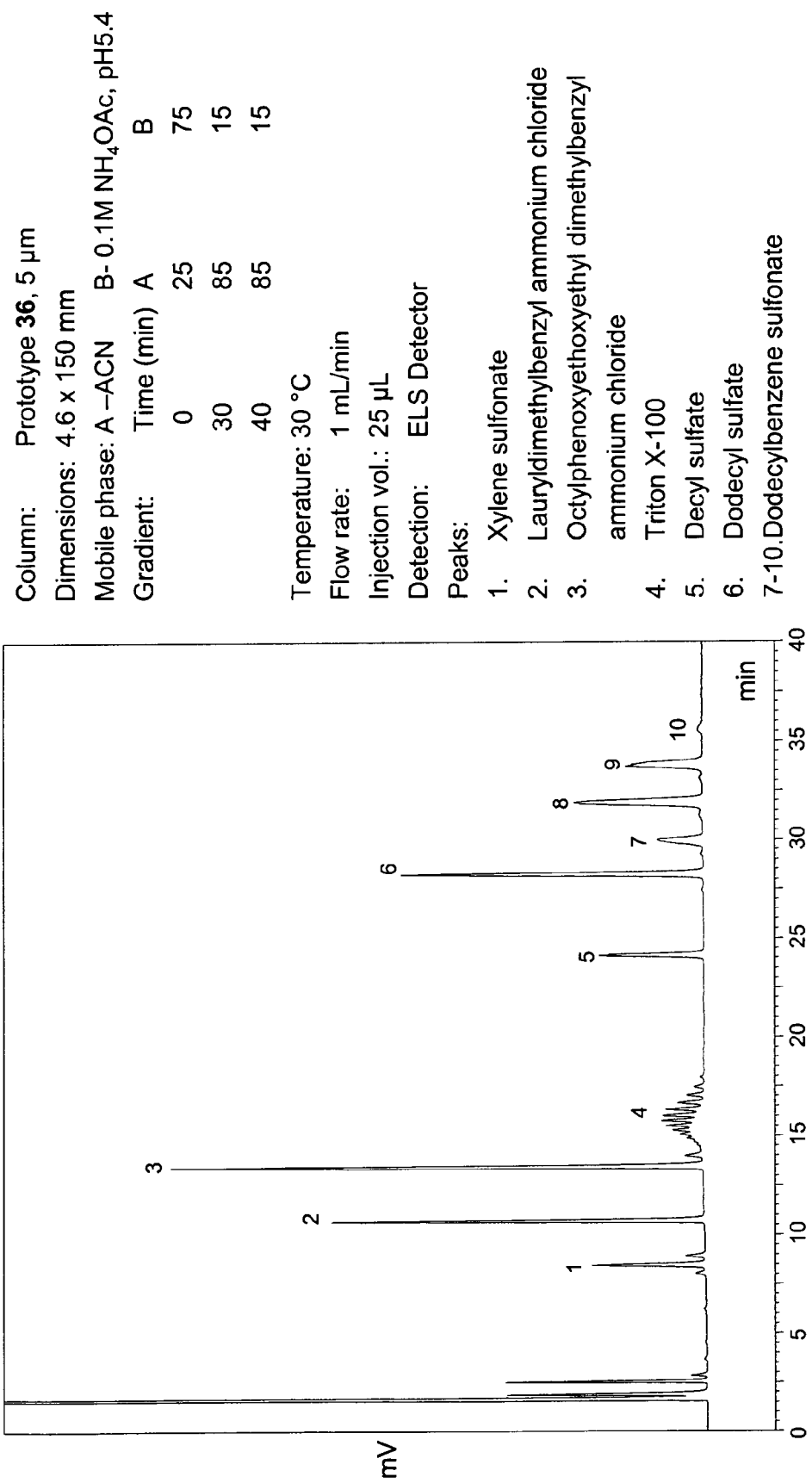
FIG. 6 illustrates separation of a number of surfactants with and a column packed with composition 36.

HPLC chromatography of a test mixture containing 7 common surfactants including two cationic surfactants (lauryldimethylbenzyl ammonium chloride and octylphenoxyethoxyethyl dimethylbenzyl ammonium chloride), four anionic surfactants (sodium salts of xylene sulfonate, dodecylbenzene sulfonate, decyl sulfate, and dodecyl sulfate) and one nonionic surfactant (Triton X-100), on composition 36 packed into 4.6×150 mm stainless steel tubes using traditional high pressure slurry techniques yielded the results illustrated in FIG. 6. The test mixture (injection volume of about 25 µL) was eluted with, $CH_3CN$ (A) and 0.1 M $NH_4OAc$ at about pH 5.8 (B) mobile phases using a gradient method (25% to 85% A in 30 min, then keep at 85% A for additional 10 min), at a flow rate of about 1 mL/min, at about 30° C. and was detected with evaporative light scattering detection (ELS).

6.9 Example 9

Chromatographic Comparison: Analysis of Ethoxylated Surfactants

Figure 7:
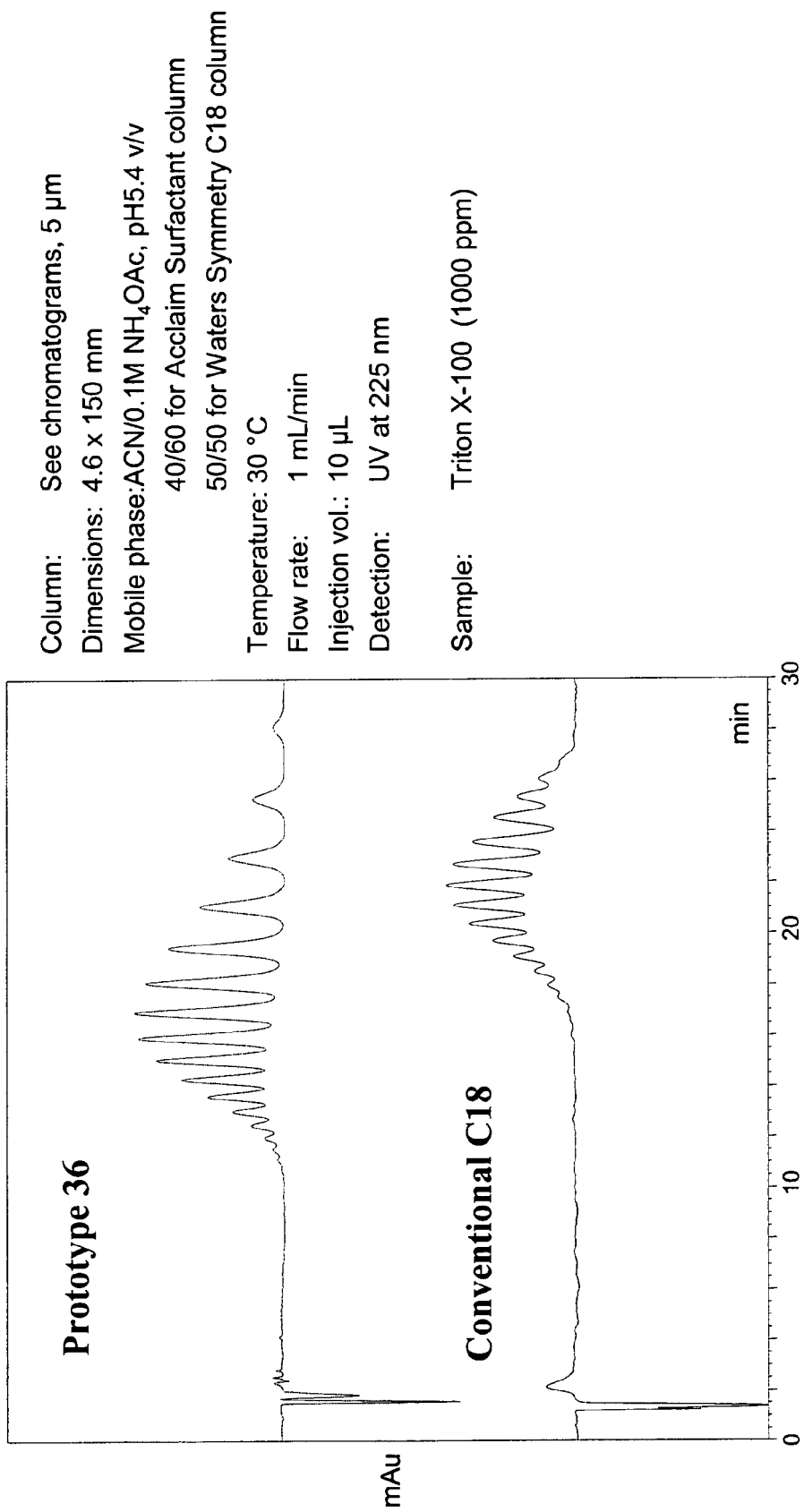
FIG. 7 illustrates the separation of Triton X-100 with a conventional C18 column and a column packed with composition 36.

As shown in FIG. 7, a column packed with composition 36 was compared with a conventional C18 column of the same column dimension (5 µm, in 4.6×150 mm stainless steel tubes) in analysis of an ethoxylated nonionic surfactant Triton X-100. The sample (injection volume of about 10 µL) was eluted with $CH_3CN$ and 0.1 M $NH_4OAc$ at about pH 5.4 (isocratic mobile phases) at a flow rate of about 1 mL/min, at about 30° C. and was detected by UV at 225 nm.

6.10 Example 10

Chromatographic Comparison: Selectivity

Figure 8:
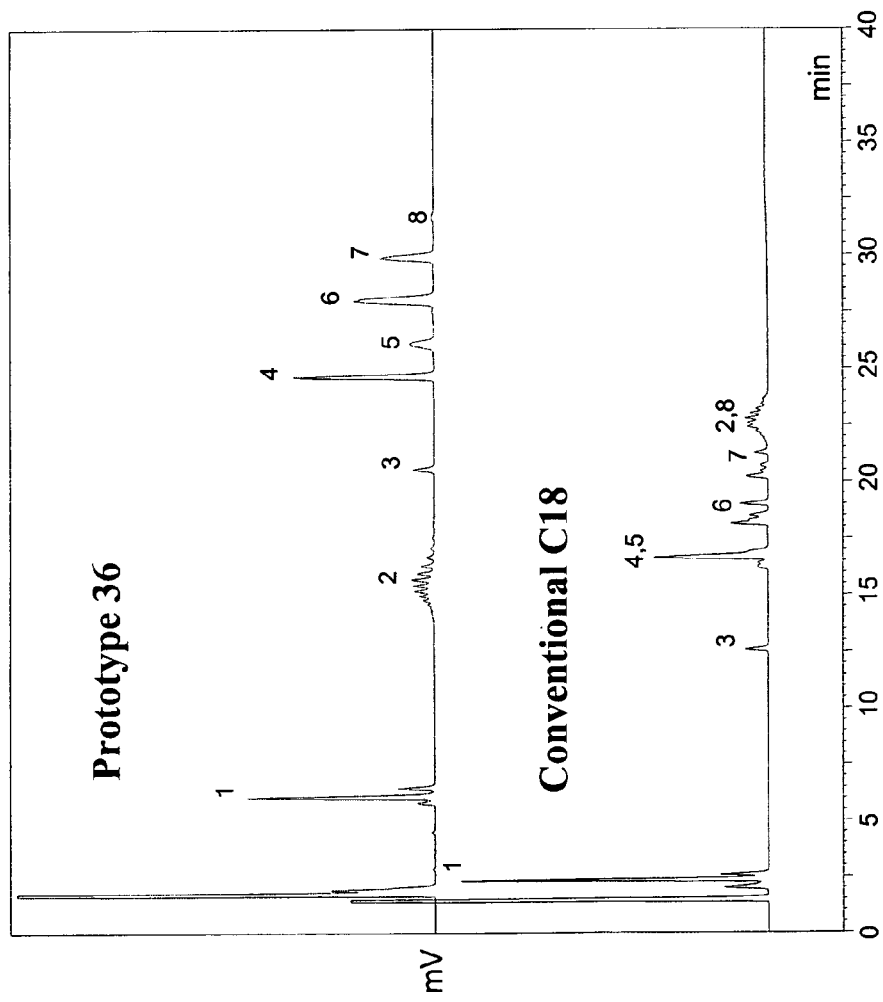
FIG. 8 illustrates the separation of a number of surfactants with a conventional C18 column and a column packed with composition 36.

HPLC chromatography of a test mixture containing 5 common surfactants including four anionic surfactants (sodium salts of xylene sulfonate, dodecylbenzene sulfonate, decyl sulfate and dodecyl sulfate) and one nonionic surfactant (Triton X-100), on composition 36 packed into 4.6×150 mm stainless steel tubes using traditional high pressure slurry techniques yielded the results illustrated in FIG. 8. The test mixture (injection volume of about 25 µL) was eluted with $CH_3CN$ (A) and 0.1 M $NH_4OAc$ at about pH 5.8 (B) mobile phases using a gradient method (25% to 85% A in 30 min, then keep at 85% A for additional 10 min) at a flow rate of about 1 mL/min at about 30° C. and detected with an evaporative light scatting detector. For comparison, the same test mixture was also chromatographed on a C18 column of the same column dimension.

6.11 Example 11

Chromatographic Comparison: Analysis of Cationic Surfactants

Figure 9:
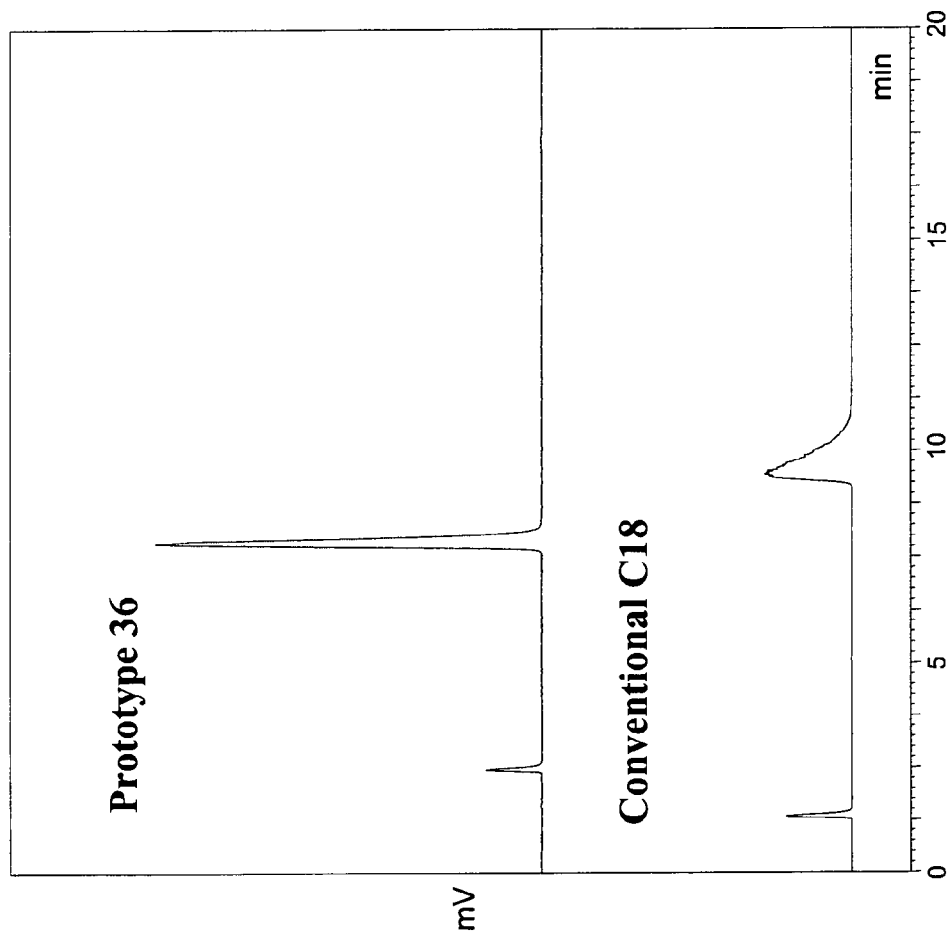
FIG. 9 illustrates the separation of lauryldimethylbenzyl ammonium chloride with a conventional C18 column and a column packed with composition 36.

As shown in FIG. 9, a column packed with composition 36 was compared with a conventional C18 column of the same column dimension (5 μm, in 4.6×150 mm stainless steel tubes) in analyzing the cationic surfactant lauryldimethylbenzyl ammonium chloride. The sample (injection volume of about 5 μL) was eluted with $CH_3CN$ and 0.1 M $NH_4OAc$ at pH 5.4 (isocratic mobile phases) at a flow rate of about 1 mL/min at about 30° C. and was detected by ELS. The column packed with composition 36 exhibits superior peak shape over the C18 column.

6.12 Example 12

Chromatographic Comparison: Analysis of Sodium Xylene Sulfonate

Figure 10:
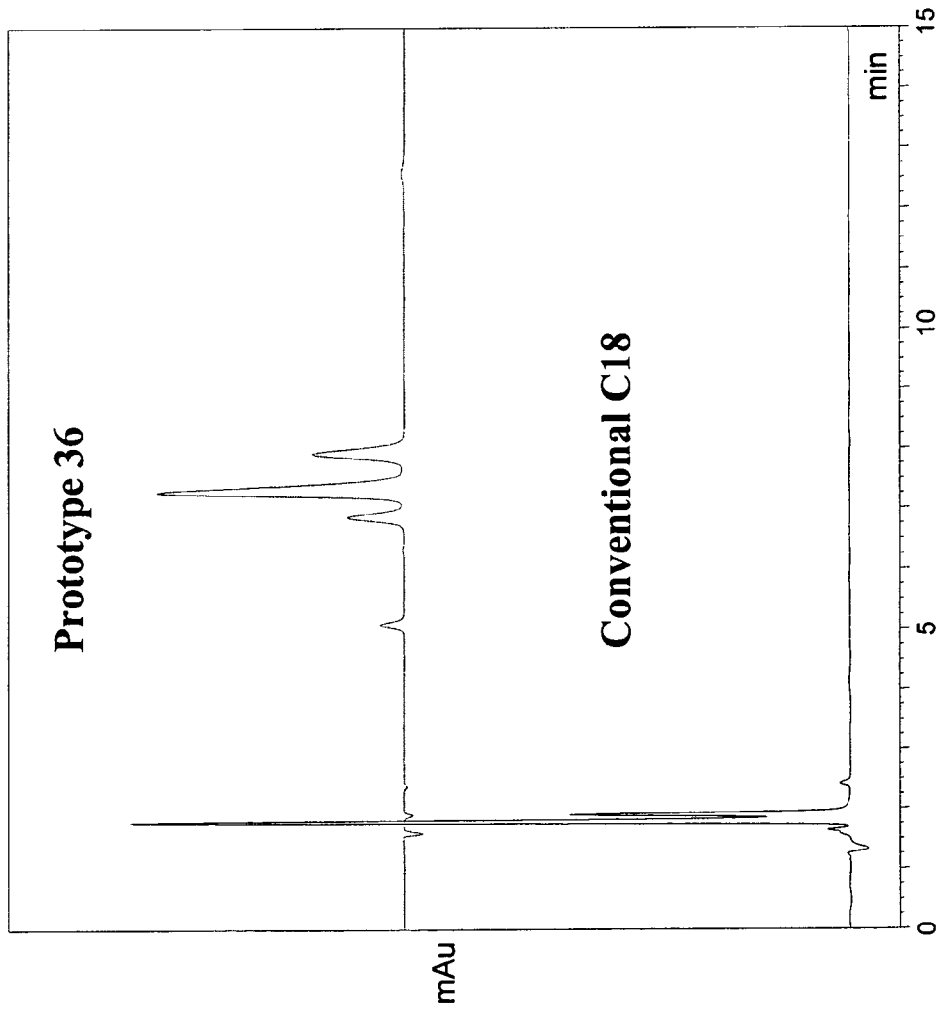
FIG. 10 illustrates the separation of sodium xylene sulfonate with a conventional C18 column and a column packed with composition 36.

As shown in FIG. 10, a column packed with composition 36 was compared with a conventional C18 column of the same column dimension (5 μm, in 4.6×150 mm stainless steel tubes) in analyzing the highly hydrophilic surfactant, sodium xylene sulfonate. The sample (injection volume of about 5 μL) was eluted with, $CH_3CN$/0.1 M $NH_4OAc$, about pH 5.4 v/v 30/70 (isocratic mobile phases) at a flow rate of about 1 mL/min, at about 30° C. and detected by UV at about 225 nm. The column packed with composition 36 exhibits excellent resolution among the isomers with decent retention times.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications and patent documents cited in this specification are herein incorporated by reference in their entirety.

What is claimed is:

1. A composition comprising a compound of structural Formula (II):

$$R^2-\underset{\underset{R^3}{|}}{\overset{\overset{R^1}{|}}{Si}}-L_1-Y \quad (II)$$

or salts, solvates or hydrates thereof, wherein $R^1$, $R^2$ and $R^3$ are independently alkyl, alkoxy, alkoxycarbonyl, alkylsulfonyloxy, amino, aryl, aryloxycarbonyl, arylsulfonyloxy, halo or hydroxyl, optionally substituted with one or more ($C_1$-$C_6$) alkyl groups, provided that at least one of $R^1$, $R^2$ and $R^3$ is not alkyl, aryl or hydroxyl;

$L_1$ is alkyldiyl, heteroalkyldiyl, aryldiyl or heteroaryldiyl; and

Y is $-C(O)N(R^4)(R^5)$, $-N(R^4)C(O)R^7$, $-N(R^4)S(O_2)R^7$, $-S(O)_2N(R^4)(R^5)$, $-OC(O)R^7$, $-OC(O)N(R^4)(R^5)$, $-N(R^4)C(O)OR^7$, $-N(R^4)C(O)N(R^5)(R^6)$ or wherein $R^4$, $R^5$ and $R^6$ are independently hydrogen, ($C_1$-$C_6$) alkyl optionally substituted with one or more hydroxy or cyano groups or ($C_5$-$C_7$) aryl optionally substituted with one or more hydroxy or cyano groups, provided that at least one of $R^4$, $R^5$ and $R^6$ is not hydrogen; and $R^7$ is ($C_2$-$C_6$) alkyl optionally substituted with one or more hydroxy or cyano groups or ($C_5$-$C_7$) aryl optionally substituted with one or more hydroxy or cyano groups;

wherein said compound is covalently bonded to a substrate, said composition further comprising a compound of structural Formula (IV) covalently bonded to said substrate:

$$R^9-\underset{\underset{R^{10}}{|}}{\overset{\overset{R^8}{|}}{Si}}-L_2-W \quad (IV)$$

wherein $R^8$, $R^2$, and $R^{10}$ are independently alkyl, alkoxy, alkoxycarbonyl, alkylsulfonyloxy, amino aryl, aryloxycarbonyl, aryloxy, arylsulfonyloxy, halo or hydroxyl optionally substituted with one or more independently selected ($C_1$-$C_6$) alkyl groups, provided that at least one of $R^1$, $R^2$ and $R^3$ is not alkyl, aryl or hydroxyl;

$L_2$ is alkyldiyl, heteroalkyldiyl, aryldiyl or heteroaryldiyl; and

W is an ionizable group and different than Y.

2. The composition of claim 1 in which the compound of structural Formula (II) is covalently bonded to the substrate by reaction of at least one of $R^1$, $R^2$ and $R^3$ with reactive groups on the substrate selected from the group consisting of silanol, alkoxysilane, halosilane and aminosilane.

3. The composition of claim 1 in which $-SiR^1(R^2)(R^3)$ is covalently bonded to another compound of said Formula II.

4. The composition of claim 1 comprising structural Forumla (V):

$$\text{Substrate}\begin{cases}-O-\underset{\underset{R^3}{|}}{\overset{\overset{R^1}{|}}{Si}}-L_1-Y \\ -O-\underset{\underset{R^{10}}{|}}{\overset{\overset{R^8}{|}}{Si}}-L_2-W. \end{cases} \quad (V)$$

5. The composition of claim 1 comprising the structure:

$$\text{Silica}\begin{cases}-O-\underset{\underset{Me}{|}}{\overset{\overset{Me}{|}}{Si}}-(CH_2)_n-N(Me)_2(Me) \\ -O-\underset{\underset{Me}{|}}{\overset{\overset{Me}{|}}{Si}}-(CH_2)_n-C(O)-N(Me)(Me). \end{cases}$$

6. The composition of claim 1 in which the substrate is a silica substrate.

7. The composition of claim 6 in which the silica substrate is silica gel.

8. The composition of claim 1 in which the substrate is glass, a sol-gel polymer or a hybrid sol-gel polymer.

9. The composition of claim 1 in a flow-through bed suitable for use in a chromatographic medium.

10. The composition of claim 9, wherein said chromatographic medium is a mixed mode chromatographic medium.

11. The composition of claim 1, wherein said compound of structural Formula (II) is bound to said substrate in a single reaction step by contacting said substrate with a precursor molecule comprising an activated silyl group, under conditions sufficient to form a covalent bond between said substrate and said precursor molecule.

12. The composition of claim 11, wherein said precursor molecule has a structure according to Formula (II) or salts, solvates or hydrates thereof:

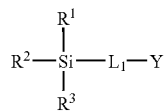
(II)

wherein
$R^1$ and $R^3$ are members independently selected from alkyl, alkoxy, alkoxycarbonyl, alkylsulfonyloxy, amino, aryl, aryloxycarbonyl, arylsulfonyloxy, halo and hydroxyl, optionally substituted with one or more independently selected ($C_1$-$C_6$) alkyl groups;

$R^2$ is a member selected from alkoxy, alkoxycarbonyl, alkylsulfonyloxy, amino, aryloxycarbonyl, arylsulfonyloxy and halo, optionally substituted with one or more independently selected ($C_1$-$C_6$) alkyl groups;

$L_1$ is alkyldiyl, heteroalkyldiyl, aryldiyl or heteroaryldiyl; and

Y is —C(O)N($R^4$)($R^5$), —N($R^4$)C(O)$R^7$, —N($R^4$)S($O_2$)$R^7$, —S(O)$_2$N($R^4$)($R^5$), —OC(O)$R^7$, —OC(O)N($R^4$)($R^5$), —N($R^4$)C(O)O$R^7$ or —N($R^4$)S($O_2$)N($R^5$)($R^6$), wherein
$R^4$, $R^5$ and $R^6$ are independently hydrogen, ($C_1$-$C_6$) alkyl optionally substituted with one or more hydroxy or cyano groups or ($C_5$-$C_7$) aryl optionally substituted with one or more hydroxy or cyano groups, provided that at least one of $R^4$, $R^5$ and $R^6$ is not hydrogen; and $R^7$ is ($C_1$-$C_6$) alkyl optionally substituted with one or more hydroxy or cyano groups or ($C_5$-$C_7$) aryl optionally substituted with one or more hydroxy or cyano groups.

* * * * *

UNITED STATES PATENT AND TRADEMARK OFFICE
CERTIFICATE OF CORRECTION

| | | |
|---|---|---|
| PATENT NO. | : 7,468,130 B2 | Page 1 of 1 |
| APPLICATION NO. | : 11/059179 | |
| DATED | : December 23, 2008 | |
| INVENTOR(S) | : Xiaodong Liu et al. | |

It is certified that error appears in the above-identified patent and that said Letters Patent is hereby corrected as shown below:

IN THE SPECIFICATION

In Col. 8, line 43, change "-OS(O)O⁻" to -- -OS(O$_2$)O⁻ --; line 53, change "C(O)OR$^{60}$" to -- -C(O)OR$^{60}$ --.

IN THE CLAIMS

In Claim 1, Col. 20, line 4, change "(C$_2$-C$_6$)" to -- (C$_1$-C$_6$) --; line 22, change "R$^8$, R$^2$, and R$^{10}$" to -- R$^8$, R$^9$, and R$^{10}$ --.

Signed and Sealed this

Thirty-first Day of August, 2010

David J. Kappos
*Director of the United States Patent and Trademark Office*